(12) United States Patent
Schmuck et al.

(10) Patent No.: US 12,419,993 B2
(45) Date of Patent: Sep. 23, 2025

(54) CARDIAC FIBROBLAST DERIVED EXTRACELLULAR MATRIX

(71) Applicant: WISCONSIN ALUMNI RESEARCH FOUNDATION, Madison, WI (US)

(72) Inventors: Eric Schmuck, Madison, WI (US); Amish Raval, Madison, WI (US); Sushmita Roy, Madison, WI (US); Tianhua Zhou, Madison, WI (US)

(73) Assignee: Wisconsin Alumni Research Foundation

( * ) Notice: Subject to any disclaimer, the term of this patent is extended or adjusted under 35 U.S.C. 154(b) by 394 days.

(21) Appl. No.: 17/929,890

(22) Filed: Sep. 6, 2022

(65) Prior Publication Data

US 2023/0072362 A1    Mar. 9, 2023

Related U.S. Application Data

(60) Provisional application No. 63/241,240, filed on Sep. 7, 2021.

(51) Int. Cl.
| | |
|---|---|
| *A61L 27/36* | (2006.01) |
| *A61K 35/12* | (2015.01) |
| *A61L 27/38* | (2006.01) |
| *C12N 5/077* | (2010.01) |

(52) U.S. Cl.
CPC ......... *A61L 27/3633* (2013.01); *A61K 35/12* (2013.01); *C12N 5/0657* (2013.01); *A61L 27/3834* (2013.01); *C12N 2533/90* (2013.01)

(58) Field of Classification Search
CPC ..... A61K 35/12; A61L 27/3687; A61L 27/54; A61L 27/3804; A61L 27/3633; A61L 27/3834; A61L 2300/414; A61L 2430/20; A61L 2300/426; C12N 5/0657; C12N 2502/1329; C12N 2533/90
See application file for complete search history.

(56) References Cited

U.S. PATENT DOCUMENTS

| | | |
|---|---|---|
| 2012/0190109 A1 | 7/2012 | Rouyer et al. |
| 2016/0331535 A1 | 11/2016 | Chachques et al. |
| 2017/0227539 A1 | 8/2017 | Deng et al. |
| 2018/0282698 A1* | 10/2018 | Hematti ......... A61K 39/46433 |
| 2019/0111113 A1 | 4/2019 | Schmuck et al. |

OTHER PUBLICATIONS

Zeng et al. Cardiac Fibroblast-Derived Extracellular Matrix Produced In Vitro Stimulates Growth and Metabolism of Cultured Ventricular Cells. Int Heart J (2013), 54, 40-44. (Year: 2013).*
Svystonyuk et al. Fibroblast growth factor-2 regulates human cardiac myofibroblast-mediated extracellular matrix remodeling. Journal of Translational Medicine (2015) 13:147. (Year: 2015).*

(Continued)

*Primary Examiner* — Sean C. Barron
(74) *Attorney, Agent, or Firm* — McDonnell Boehnen Hulbert & Berghoff LLP (57) ABSTRACT

The disclosure generally relates to methods, cells, and compositions for preparing cardiac extracellular matrix. In particular, provided herein are methods for preparing a cardiac extracellular matrix using SUSD2 High fibroblasts and SUSD2 High myofibroblasts.

22 Claims, 8 Drawing Sheets

(56) References Cited

OTHER PUBLICATIONS

Zhang et al. Downregulation of endometrial mesenchymal marker SUSD2 causes cell senescence and cell death in endometrial carcinoma cells. PLoS One. Aug. 25, 2017;12(8):e0183681. (Year: 2017).*
Watson et al. Multiple Functions of Sushi Domain Containing 2 (SUSD2) in Breast Tumorigenesis. Mol Cancer Res. Jan. 2013;11(1):74-85. (Year: 2013).*
Cheng et al. SUSD2 is frequently downregulated and functions as a tumor suppressor in RCC and lung cancer. Tumour Biol. Jul. 2016;37(7):9919-30. (Year: 2016).*
Bredencamp et al. The Cell-Surface Marker Sushi Containing Domain 2 Facilitates Establishment of Human Naive Pluripotent Stem Cells. Stem Cell Reports. Jun. 11, 2019;12(6):1212-1222, epub Apr. 25, 2019. (Year: 2019).*
J. Baum and H.S. Duffy. Fibroblasts and Myofibroblasts: What Are We Talking About?J Cardiovasc Pharmacol (2011), 54(4), 376-379. (Year: 2011).*
International Search Report and Written Opinion for PCT/US2022/75975, mailed Nov. 30, 2022.
Schmuck et al. "Cultured cardiac fibroblasts and myofibroblasts express Sushi Containing Domain 2 and assemble a unique fibronectin rich matrix". Exp Cell Res. 399(2):112489, (Feb. 2021).

* cited by examiner

CARDIAC FIBROBLAST DERIVED EXTRACELLULAR MATRIX

CROSS-REFERENCE TO RELATED APPLICATIONS

This application claims priority to U.S. Provisional Patent Application No. 63/241,240, filed Sep. 7, 2021, the disclosure of which is hereby incorporated by reference in its entirety

STATEMENT REGARDING FEDERALLY SPONSORED RESEARCH

This invention was made with government support under CA014520 awarded by the National Institutes of Health. The government has certain rights in the invention.

FIELD OF THE DISCLOSURE

The disclosure generally relates to methods, cells, and compositions for preparing a cardiac extracellular matrix. In particular, provided herein are methods for preparing a cardiac extracellular matrix using SUSD2 High fibroblasts and SUSD2 High myofibroblasts.

BACKGROUND

Cardiac fibroblasts (CF) and myofibroblasts (CMF) are cells of mesenchymal origin that adhere to plastic, secrete matricellular proteins and are involved in organ development, wound healing, fibrosis, immunomodulation and extracellular matrix (ECM) assembly. Isolation and culture expansion of CF and CMF for the purpose of matrix production has potential utility in tissue engineering and regenerative medicine. For example, fibronectin-rich matrix scaffolds assembled from cultured CF can be used to deliver mesenchymal stromal cells to the injured myocardium. In addition, matrix derived from cultured human CF/CMF converts monocytes into macrophages that express interesting anti-inflammatory and pro-angiogenic properties. Expanded investigations involving these bioengineered matrices requires careful characterization of cultured CF and CMF for quality control purposes prior to scaling up manufacturing. Many studies define human CF and CMF by simple morphometric geometry, plastic adherence and the ability to assemble ECM. However, these features are non-specific. Other cells types such as mesenchymal stromal cells (MSC) and pericytes are morphometrically similar and readily adherent to plastic. Furthermore, certain parenchymal cells and immune cells produce ECM under certain conditions. Several markers have been identified on human CF and CMF. Sushi Containing Domain 2 (SUSD2) has recently been identified as a new cell marker for CF.

SUMMARY

Provided herein is a method for preparing a cardiac extracellular matrix, comprising: (a) selecting SUSD2 High fibroblasts from a population of cardiac fibroblasts; and (b) plating the SUSD2 High fibroblasts into a culture having a cell density of 100,000 to 500,000 cells per $cm^2$, wherein the SUSD2 High fibroblasts secrete a cardiac extracellular matrix that is attached to the surface on which the SUSD2 High fibroblasts are plated.

Also provided herein is a method for preparing a cardiac extracellular matrix, comprising: (a) expanding cardiac fibroblasts in culture to obtain a population of cardiac fibroblasts; (b) selecting SUSD2 High fibroblasts from the population of cardiac fibroblasts; and (c) plating the SUSD2 High fibroblasts into a culture having a cell density of 100,000 to 500,000 cells per $cm^2$, wherein the SUSD2 High fibroblasts secrete a cardiac extracellular matrix that is attached to the surface on which the SUSD2 High fibroblasts are plated.

Also provide herein is a method for preparing a cardiac extracellular matrix, comprising: (a) selecting SUSD2 High myofibroblasts from a population of cardiac myofibroblasts; and (b) plating the SUSD2 High myofibroblasts into a culture having a cell density of 100,000 to 500,000 cells per $cm^2$, wherein the SUSD2 High myofibroblasts secrete a cardiac extracellular matrix that is attached to the surface on which the SUSD2 High myofibroblasts are plated.

Also provide herein is a method for preparing a cardiac extracellular matrix, comprising: (a) expanding cardiac myofibroblasts in culture to obtain a population of cardiac myofibroblasts; (b) selecting SUSD2 High myofibroblasts from the population of cardiac myofibroblasts; and (c) plating the SUSD2 High myofibroblasts into a culture having a cell density of 100,000 to 500,000 cells per $cm^2$, wherein the SUSD2 High myofibroblasts secrete a cardiac extracellular matrix that is attached to the surface on which the SUSD2 High myofibroblasts are plated.

Also provided herein is a method of generating a population of SUSD2 High fibroblasts, the method comprising selecting SUSD2 High fibroblasts from a population of cardiac fibroblasts to yield a population of SUSD2 High fibroblasts.

Also provided herein is a method of generating a population of SUSD2 High fibroblasts, the method comprising, (a) expanding cardiac fibroblasts in culture to obtain a population of cardiac fibroblasts; and (b) selecting SUSD2 High fibroblasts from the population of cardiac fibroblasts to yield a population of SUSD2 High fibroblasts.

Also provided herein is a method of generating a population of SUSD2 High myofibroblasts, the method comprising, selecting SUSD2 High myofibroblasts from the population of cardiac myofibroblasts to yield a population of SUSD2 High myofibroblasts.

Also provided herein is a method of generating a population of SUSD2 High myofibroblasts, the method comprising, (a) expanding the cardiac myofibroblasts in culture to obtain a population of cardiac myofibroblasts; and (b) selecting SUSD2 High myofibroblasts from the population of cardiac myofibroblasts to yield a population of SUSD2 High myofibroblasts.

BRIEF DESCRIPTION OF THE DRAWINGS

FIG. 4A-4H. shows the differences between cytokine secretome analysis for SUSD2 High/Low cell populations. The cytokines tested were (FIG. 4A) IL-6; (FIG. 4B) Ang-1; (FIG. 4C) Ang-2; (FIG. 4D) PGIF; (FIG. 4E) bFGF; (FIG. 4F) IL-8; (FIG. 4G) PECAM; and (FIG. 4H) VEGF. Cardiac fibroblasts/myofibroblasts were sorted based on SUSD2 MFI expression (Low <500 MFI; High >500 MFI), equal numbers of SUSD2 High/Low cells were plated and cultured under standard culture conditions for 3 days. Media was sampled and analyzed for multiple analytes (cytokines). Significant differences in several cytokines were detected.

DETAILED DESCRIPTION

The disclosure generally relates to methods, cells, and compositions for preparing cardiac extracellular matrix. In particular, provided herein are methods for preparing a cardiac extracellular matrix using SUSD2 High fibroblasts and SUSD2 High myofibroblasts.

All publications, including but not limited to patents and patent applications, cited in this specification are herein incorporated by reference as though set forth in their entirety in the present application.

In particular embodiments provided herein is a method for preparing a cardiac extracellular matrix, comprising: (a) selecting SUSD2 High fibroblasts from a population of cardiac fibroblasts; and (b) plating the SUSD2 High fibroblasts into a culture having a cell density of 100,000 to 500,000 cells per $cm^2$, wherein the SUSD2 High fibroblasts secrete a cardiac extracellular In particular embodiments provided herein is a method for preparing a cardiac extracellular matrix, comprising: (a) expanding cardiac fibroblasts in culture to obtain a population of cardiac fibroblasts; (b) selecting SUSD2 High fibroblasts from the population of cardiac fibroblasts; and (c) plating the SUSD2 High fibroblasts into a culture having a cell density of 100,000 to 500,000 cells per $cm^2$, wherein the SUSD2 High fibroblasts secrete a cardiac extracellular matrix that is attached to the surface on which the SUSD2 High fibroblasts are plated.

In particular embodiments provided herein is a method for preparing a cardiac extracellular matrix, comprising: (a) selecting SUSD2 High myofibroblasts from a population of cardiac myofibroblasts; and (b) plating the SUSD2 High myofibroblasts into a culture having a cell density of 100,000 to 500,000 cells per $cm^2$, wherein the SUSD2 High myofibroblasts secrete a cardiac extracellular matrix that is attached to the surface on which the SUSD2 High myofibroblasts are plated.

In particular embodiments provided herein is a method for preparing a cardiac extracellular matrix, comprising: (a) expanding cardiac myofibroblasts in culture to obtain a population of cardiac myofibroblasts; (b) selecting SUSD2 High myofibroblasts from the population of cardiac myofibroblasts; and (c) plating the SUSD2 High myofibroblasts into a culture having a cell density of 100,000 to 500,000 cells per $cm^2$, wherein the SUSD2 High myofibroblasts secrete a cardiac extracellular matrix that is attached to the surface on which the SUSD2 High myofibroblasts are plated.

In particular embodiments provided herein is a method of generating a population of SUSD2 High fibroblasts, the method comprising selecting SUSD2 High fibroblasts from a population of cardiac fibroblasts to yield a population of SUSD2 High fibroblasts.

In particular embodiments provided herein is a method of generating a population of SUSD2 High fibroblasts, the method comprising, (a) expanding cardiac fibroblasts in culture to obtain a population of cardiac fibroblasts; and (b) selecting SUSD2 High fibroblasts from the population of cardiac fibroblasts to yield a population of SUSD2 High fibroblasts.

In particular embodiments provided herein is a method of generating a population of SUSD2 High myofibroblasts, the method comprising, selecting SUSD2 High myofibroblasts from a population of cardiac myofibroblasts to yield a population of SUSD2 High myofibroblasts.

In particular embodiments provided herein is a method of generating a population of SUSD2 High myofibroblasts, the method comprising, (a) expanding cardiac myofibroblasts in culture to obtain a population of cardiac myofibroblasts; and (b) selecting SUSD2 High myofibroblasts from the population of cardiac myofibroblasts to yield a population of SUSD2 High myofibroblasts.

Sushi Containing Domain 2 (SUSD2) is an 822 amino acid type I membrane protein with transmembrane domain and functional domains inherent to adhesion molecules. This marker is variably expressed on endometrial mesenchymal stem cells, breast and lung cancer cells, and human embryonic stem cells.

As used herein, "high" means that the cells are characterized by a high level of expression of SUSD2. In particular embodiments, SUSD2 positive fibroblasts or myofibroblasts are characterized as "high" when the cells have a median fluorescence intensity (MFI) >500. In particular embodiments, SUSD2 positive fibroblasts or myofibroblasts are characterized as "low" when the cells have a median fluorescence intensity (MFI)<500.

In particular embodiments, the cardiac fibroblasts or myofibroblast are expanded by culturing the cells under conditions appropriate for expansion to produce a population of cardiac fibroblasts or myofibroblasts. In one embodiment, the cells are cultured in high glucose MCDB131+10% FBS and 1% penicillin/streptomycin at 37° C. in a 5% $CO_2$ 100% humidity atmosphere for 10-14 days. In particular embodiments, selecting SUSD2 High fibroblasts or myofibroblasts from the population of cardiac fibroblasts or myofibroblasts to yield a population of SUSD2 High myofibroblasts includes flow cytometry. In particular embodiments, selecting SUSD2 High fibroblasts or myofibroblasts from the population of cardiac fibroblasts or myofibroblasts to yield a population of SUSD2 High myofibroblasts is based on overexpression of SUSD2 gene.

In particular embodiments, the cardiac fibroblasts or myofibroblasts are isolated from a cardiac tissue. The cardiac fibroblasts and myofibroblasts may be isolated using methods known in the art. In particular embodiments, the cardiac fibroblasts or myofibroblasts are differentiated from an induced pluripotent stem cell. An "induced pluripotent stem cells" or "iPS cells" means a pluripotent cell or population of pluripotent cells that are produced in vitro from non-pluripotent cells such as differentiated somatic cells by inducing expression of certain potency-determining factors therein, that may vary with respect to their differentiated somatic cell of origin, that may vary with respect to a specific set of potency-determining factors, and that may vary with respect to culture conditions used to isolate them, but nonetheless are substantially genetically identical to their respective differentiated somatic cell of origin and display characteristics similar to higher potency cells, such as ESCs.

In particular embodiments, the cardiac extracellular matrix has a thickness of 20-500 μm that is attached to the surface on which the expanded cardiac fibroblasts are plated. In other embodiments, the cardiac ECM may have a thickness of 30-200 μm or 50-150 μm.

In some embodiments, the cardiac ECM includes the structural proteins fibronectin, collagen type I, collagen type III, and elastin, and may include other structural proteins as well. In some embodiments, the cardiac ECM includes the structural protein collagen type V.

In addition to the structural proteins, the cardiac ECM may include matricellular proteins, such as growth factors and cytokines, as well as other substance. Non-limiting examples of other proteins that may be found in the cardiac ECM include latent transforming growth factor beta 1 (LTGFB-1), latent transforming growth factor beta 2 (LTGFB-2), connective tissue growth factor (CTGF), secreted protein acidic and rich in cysteine (SPARC), versican core protein (VCAN), galectin 1, galectin 3, matrix gla protein (MGP), sulfated glycoprotein 1, protein-lysine 6-oxidase, and biglycan. In some embodiments, the ECM may optionally include one or more of transforming growth factor beta 1 (TGFB-1), transforming growth factor beta 3 (TGFB-3), epidermal growth factor-like protein 8, growth/differentiation factor 6, granulins, galectin 3 binding protein, nidogen 1, nidogen 2, decorin, prolargin, vascular endothelial growth factor D (VEGF-D), Von Willebrand factor A1, Von Willebrand factor A5 A, matrix metalprotease 14, matrix metalprotease 23, platelet factor 4, prothrombin, tumor necrosis factor ligand superfamily member 11, and glia derived nexin.

In particular embodiments, the method disclosed herein further comprises contacting the secreted cardiac extracellular matrix with ethylenediaminetetraaceticacid (EDTA), whereby the cardiac extracellular matrix becomes detached from the surface, forming a free floating bioscaffold.

In some embodiments, the bioscaffold that is made from the ECM has a thickness of 20-500 μm. In some embodiments, the bioscaffold has a thickness range of 30-200 μm or of 50-150 μm.

Figure 6:
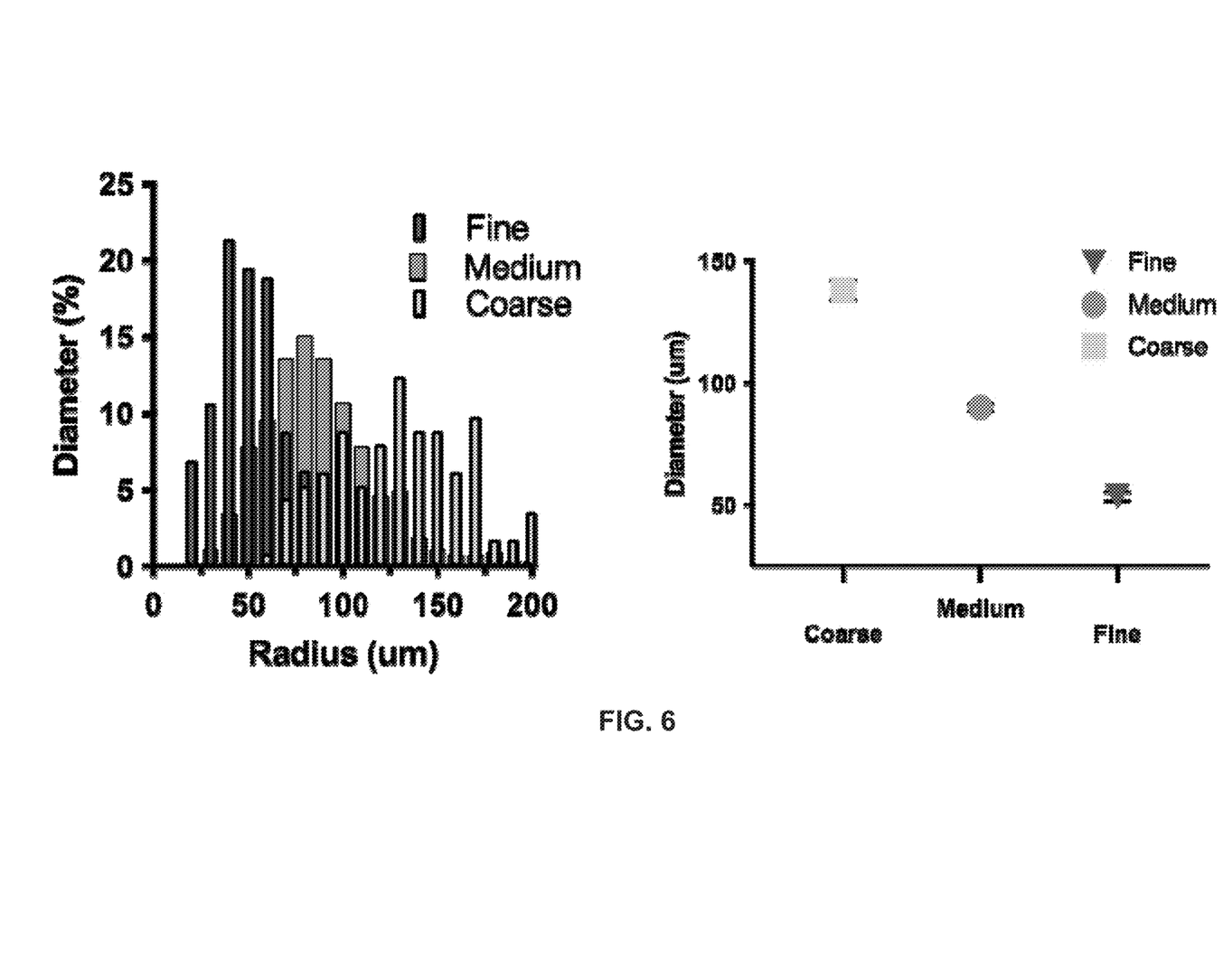
FIG. 6 illustrates that injectable CF/CMF-ECM can be milled to defined specifications by tuning the milling protocol. 3 different grind sizes were produced (Coarse: 138+/−4.0 mm, Medium: 90+/−1.5 mm, and Fine, 53+/−1.7 mm).
Figure 7:
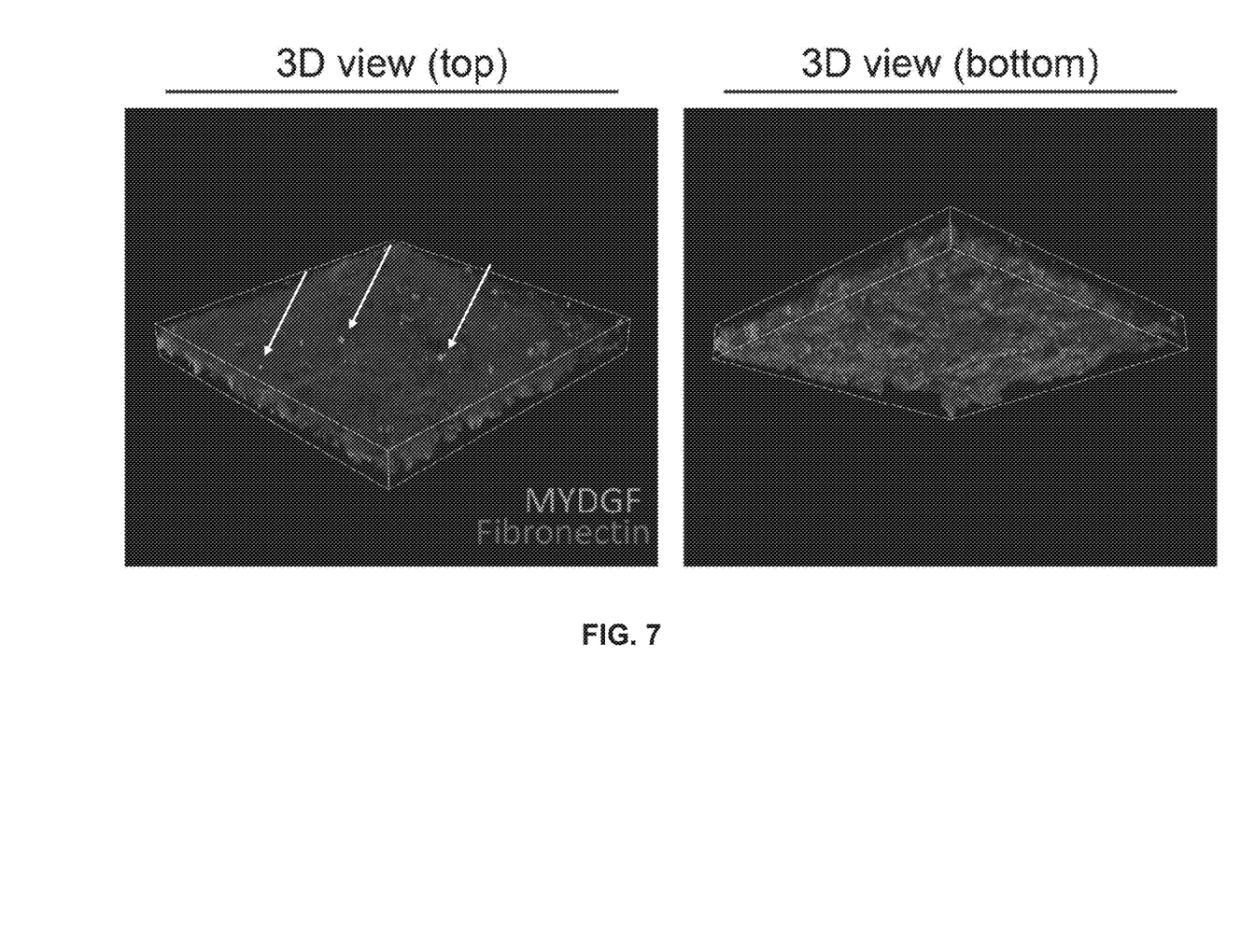
FIG. 7 illustrates a photomicrograph showing that Myeloid Derived Growth Factor (MYDGF) directly binds to the ECM disclosed herein. The arrows identify the MYDGF located within the fibronectin of the ECM.

In some embodiments, the ECM is formulated as an injectable formulation. For example, the ECM is lyophilized and milled using a pharmaceutical bead mill to specific particle sizes that are suitable for injection as a suspension (FIG. 6). In other examples, the ECM can be formulated for injection by flash freezing and milling.

In some embodiments, the cardiac ECM is decellularized to remove any remaining cardiac fibroblasts from the ECM. Any decellularizing agent may be used to decellularize the cardiac ECM. Non-limiting examples of decellurizing agents known in the art include enzymatic agents, such as trypsin, endonucleases, or exonucleases; chemical agents, such as alkaline or acid solutions, hypertonic or hypertonic solutions, ethylenediaminetetraacetic acid (EDTA), ethylene glycol tetraacetic acid (EGTA), ammonium hydroxide, and peracetic acid; nonionic detergents, such as octylphenol ethylene oxide (Triton™-X 100); ionic detergents, such as sodium dodecyl sulfate (SDS) and polyether sulfonate (Triton™-X 200); and zwitterionic detergents, such as 3-[(3-cholamidopropyl)dimethylammonio]-1-propanesulfonate (CHAPS), sulfobetaine-10 and -16, and tri(n-butyl)phosphate.

In one embodiment, decellularization is performed by contacting the cardiac ECM with peracetic acid (PAA) and subsequently rinsing the cardiac extracellular matrix with water. In one embodiment, decellularization is performed by contacting the secreted cardiac extracellular matrix with Tri-N-Butyl-Phosphate (TNBP) and octylphenol ethylene oxide (Triton™ X-100) and subsequently rinsing the cardiac extracellular matrix with water. Alternatively, decellularization is performed by contacting the secreted cardiac extracellular matrix with ammonium hydroxide (AH) and octylphenol ethylene oxide (Triton™ X-100) and subsequently rinsing the cardiac extracellular matrix with water.

In some embodiments, the ECM or bioscaffold may be seeded using methods that are known in the art with one or more cells that are therapeutic for cardiac disease or injury. Examples of therapeutic cells types that could be used for seeding include without limitation skeletal myoblasts, embryonic stem cells (ES), induced pluripotent stem cells (iPS), multipotent adult germline stem cells (maGCSs), bone marrow mesenchymal stem cells (BMSCs), very small embryonic-like stem cells (VSEL cells), endothelial progenitor cells (EPCs), cardiopoietic cells (CPCs), cardiosphere-derived cells (CDCs), multipotent Is/1+ cardiovascular progenitor cells (MICPs), epicardium-derived progenitor cells (EPDCs), adipose-derived stem cells, human mesenchymal stem cells (derived from iPS or ES cells), human mesenchymal stromal cells (derived from iPS or ES cells) skeletal myoblasts, exosomes, or combinations thereof.

In some embodiments, the ECM or bioscaffold binds bioactive proteins including cytokines and growth factors. In some embodiments, the ECM or bioscaffold may be seeded with a bioactive protein such as cytokine or growth factor. In some embodiments, the ECM or bioscaffold may be seeded with Myeloid Derived Growth Factor (MYDGF). The seeded ECM or bioscaffold may be used to deliver the bioactive proteins into the heart or other tissue to increase local tissue concentrations.

In some embodiments, the ECM or bioscaffold may be used for gene delivery. For example, the ECM or bioscaffold may be seeded with an RNA plasmid or a DNA plasmid for delivery to tissues as a therapeutic.

In some embodiments, the ECM or bioscaffold is used by itself as a therapeutic agent. For example, the ECM or bioscaffold is delivered to heart tissue to improve cardiac function and/or reduce deleterious remodeling.

As utilized in accordance with the present disclosure, unless otherwise indicated, all technical and scientific terms shall be understood to have the same meaning as commonly understood by one of ordinary skill in the art. Unless otherwise required by context, singular terms shall include pluralities and plural terms shall include the singular.

Without limiting the disclosure, a number of embodiments of the disclosure are described below for purpose of illustration.

EXAMPLES

The Examples that follow are illustrative of specific embodiments of the disclosure, and various uses thereof. They are set forth for explanatory purposes only and should not be construed as limiting the scope of the disclosure in any way.

Example 1: SUSD2$^{High}$ and SUSD2$^{Low}$ Cardiac Fibroblast-Derived Extracellular Matrix Materials & Methods Human cardiac fibroblast isolation and culture. Donor human hearts (n=6, 3 male, 3 female) that were considered healthy but went unmatched for transplant were obtained. At the time of harvest, hearts were aseptically excised, perfused and stored in cold cardioplegia solution, and transported on ice. Hearts were processed 4-6 h post explant. Epicardial fat was removed and approximately 20-30 g of left ventricular free wall was minced and transferred into 4 gentleMACS C tubes (Miltenyi Biotec, Bergisch Gladbach, Germany). 10 ml of digestion media containing DMEM (Corning, Corning, NY) and 1.25 mg Liberase™ (Roche, Basel, Switzerland) was added to each tube. The sample was homogenized with a gentleMACS dissociator (Miltenyi Biotec, Bergisch Gladbach, Germany), incubated at 37° C. for 30 min with constant agitation, and the process was repeated for a total of 1-h tissue dissociation. Heart samples were sieved through a 200 m filter and then centrifuged at 1000×g for 20 min. The cell pellet was suspended in 20 ml complete media (MCDB 131 with 10% FBS, 1 ng/ml basic fibroblast growth factor (bFGF), 5 g/ml insulin, 10 g/ml ciprofloxacin and 2.5 mg/ml amphotericin B) and plated into two T75 flasks. Cells were permitted to attach for 2 h. Non-adherent cells were removed by washing in phosphate-buffered saline (PBS). Finally, complete media was added and the cells were cultured at 37° C., 5% CO2, and 100% humidity, and passaged once they were ~90% confluent. All procedures were performed under aseptic conditions. As a comparator, 3 dermal fibroblast lines (2 male, 1 female) were purchased from Lonza catalog #CC-2511 and cultured according to manufacturers' protocols.

Human cardiac fibroblast-derived matrix production. Human CMF at passage 3-6 were suspended in high glucose DMEM with 10% fetal bovine serum (FBS) (Peak Serum, Wellington, CO) and 10 g/ml ciprofloxacin, 2.5 mg/ml amphotericin B and plated at $1.1 \times 10^5$ to $2.2 \times 10^5$ cells per cm$^2$ and maintained under standard culture conditions with media replaced every 2-3 days for 7-10 days. CF were lifted off the plate as a contiguous sheet by contact with 2 mM EDTA at 37° C. and gentle agitation. The resulting sheets were denuded of cells by four alternating washes of hypo/hypertonic PBS (15 min each) followed by incubation in 0.1% Tri-N-Butyl-phosphate, 1% Triton-X 100 in hypotonic PBS for 72 h at 4° C. with constant gentle agitation. Scaffolds were rinsed in PBS then 100% Ethanol (×2). Residual DNA was removed by incubation with 100 U/ml Benzonase solution for 20 h at 37° C., followed by 100% ethanol rinse (×2), PBS (3×15 min), and molecular grade water (2 h). Scaffolds were stored in PBS at 4° C.

Flow cytometry characterization. CF and CMF passage 0-4 were cultured to 80% confluency and collected by lifting with 1× TrypLE select (Gibco-life technologies, Cat. #12563-029). Single cell suspensions were stained for PE-anti-SUSD2 (Clone W3D5; Biolegend) or purified anti-SUSD2 (Biolegend, Clone #W5C5) for flow cytometry analysis. Cardiac fibroblasts were sorted with flow cytometry based on their expression of SUSD2 (SUSD2 High (MFI >500) and SUSD2 Low (MFI<500)). All gating was done based on their unstained control. Samples were run on BD FACS Aria II.

SUSD2-PE sorting was standardized on BD FACS Aria II. The sensitivity of SUSD2-PE was optimized based on the unstained and stained controls. Then rainbow beads were collected (Spherotech, catalog #Cat. RFP-30-5A) and the MFI of Rainbow beads was used as the target for sensitivity going forward. In consecutive experiments Rainbow beads were run and adjusted voltage to meet the Target MFI. This allowed to standardize gate placements and compare expression levels of SUSD2-PE using MFI from sample to sample and run to run.

SUSD2 immunofluorescence imaging of matrix producing. CF CMF and DF (100,000 cells per well) were stained with phycoerythrin (PE) conjugated SUSD2 primary antibody (Clone W3C5, Biolegend). The cells were washed and further fixed with 1% PFA (Paraformaldehyde solution 4% in PBS; ChemCruz, Cat. #sc-281,692) at room temperature in the dark for 30 min. The cells were permeabilized with 0.1% Triton X-100 in PBS for 10 min at room temperature and then blocked with 3% BSA solution for 20 min. Cells were further co-stained with Alexa Fluor 488 conjugated Vimentin (Cat. #IC2105G R&D Systems) overnight at 4° C. Cells were rinsed with 1×PBS. Washed cells were briefly treated with 4',6-diamidino-2-phenylindole (DAPI) (10 g/ml) and washed with 1×PBS. The stained cells were imaged with an EVOS microscope, and images were acquired using 20× and 40× objectives.

Cytokine Secretome Analysis. To test for differences between SUSD2 High/Low cell populations, a cytokine secretome analysis was done using a LegendPlex assay. The assay used antibody beads tagged with fluorochromes to detect secreted cytokines. Cardiac fibroblasts/myofibroblasts were then sorted based on SUSD2 MFI expression (Low <500 MFI; High >500 MFI), equal numbers of SUSD2 High/Low cells were plated and cultured under standard culture conditions for 3 days. Media was sampled and analyzed for multiple cytokines.

Results

Figure 1:
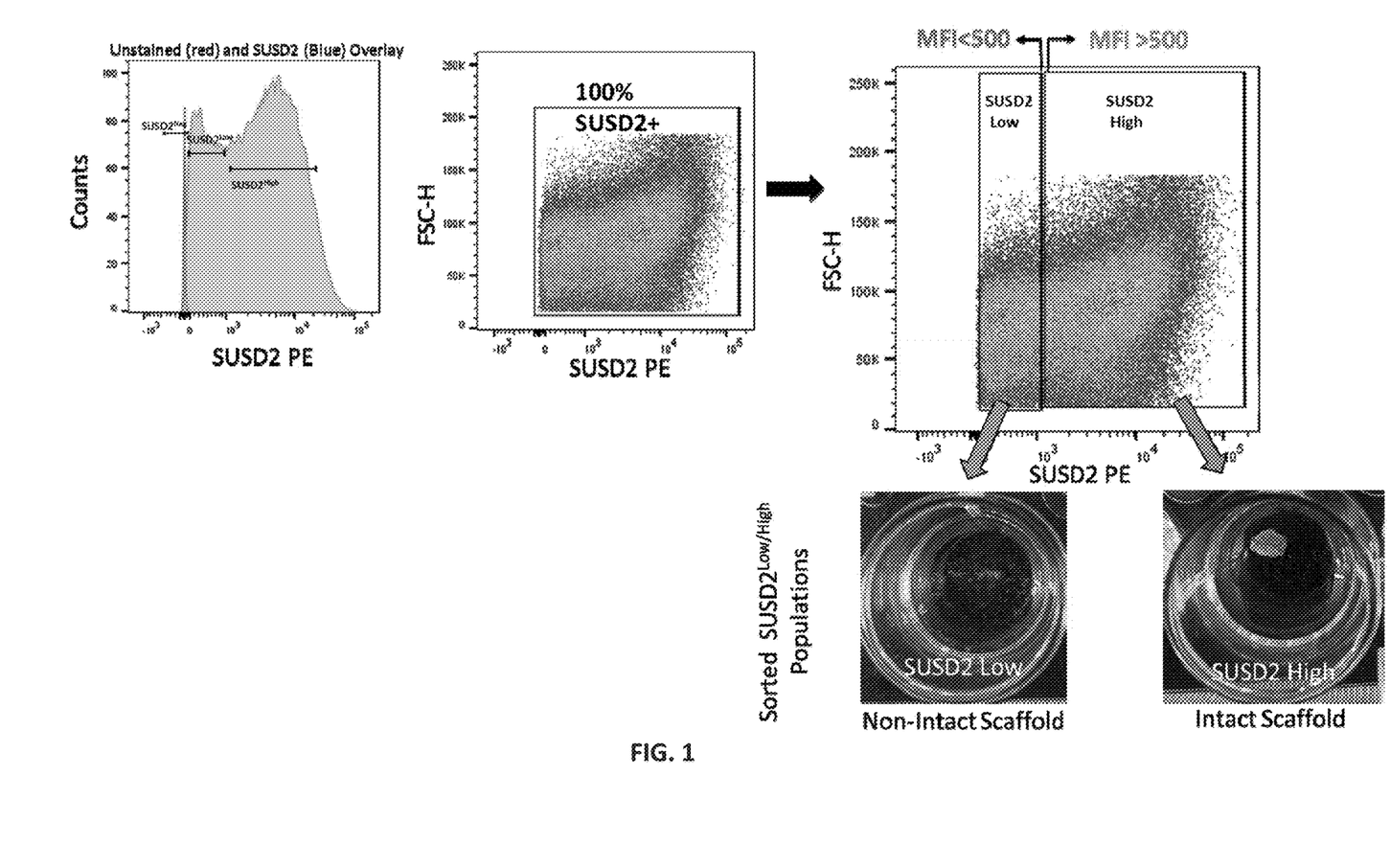
FIG. 1 shows that SUSD2 can be used as a marker of cardiac fibroblast derived extracellular matrix production. Human cardiac fibroblast cell strain was stained for SUSD2. 98.8% of cells expressed SUSD2, cells were sorted into SUSD2 High (Median Fluorescent Intensity (MFI) >500) and SUSD2 Low (MFI<500) and plated in high density and cultured for 10 days. SUSD2 High cardiac fibroblasts produced intact cardiac fibroblast derived extracellular matrix while SUSD2 Low cells did not produce an intact matrix.
Figure 2:
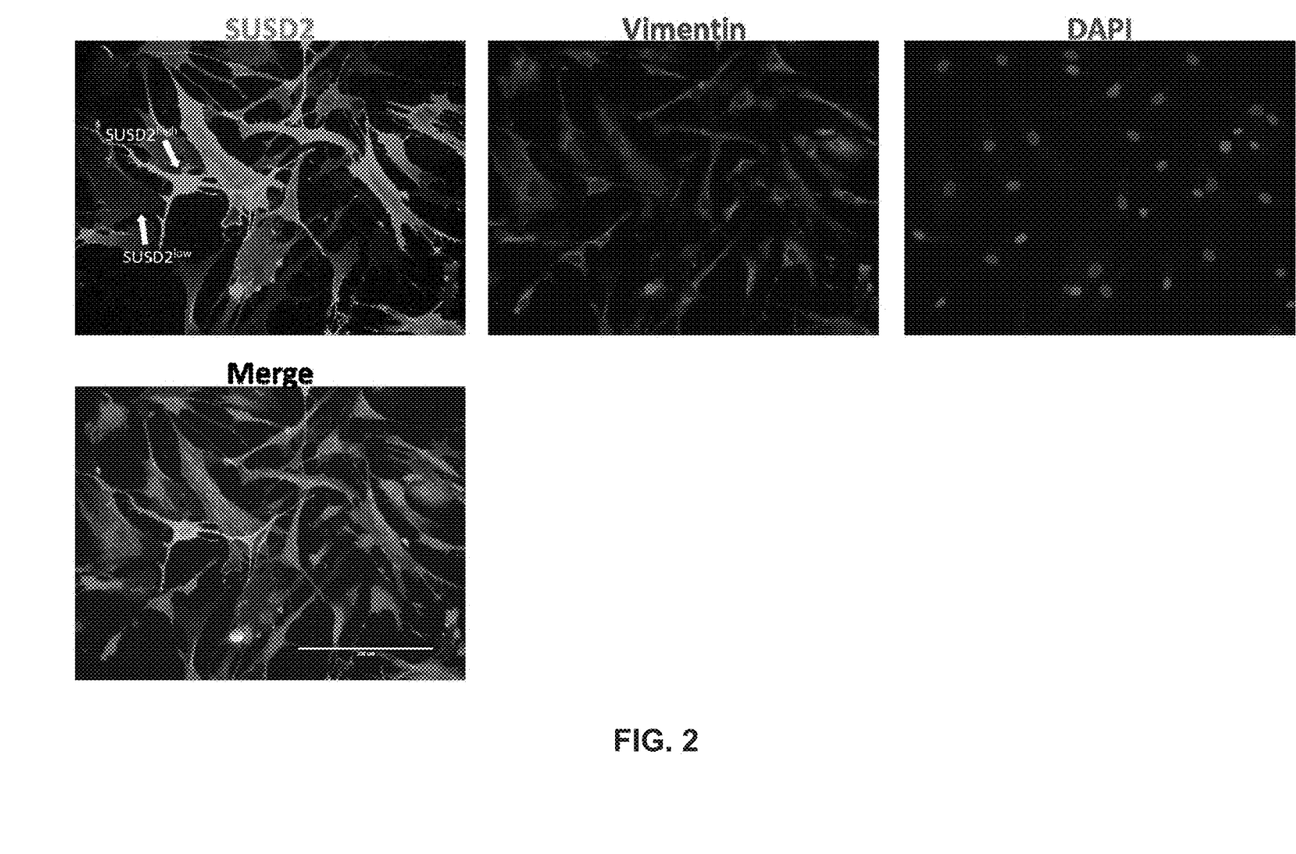
FIG. 2 shows immunohistochemistry images of cardiac fibroblasts co-expressing SUSD2 and Vimentin. Representative high and low SUSD2 expressing cells are indicated with arrows.

As demonstrated in FIG. 1, SUSD2 can be used as a marker of cardiac fibroblast derived extracellular matrix production. Human cardiac fibroblast cell strain was stained for SUSD2. 98.8% of cells expressed SUSD2, cells were sorted into SUSD2 High (MFI >500) and SUSD2 Low (MFI<500) and plated in high density (i.e., 100,000-500,000 cells/cm$^2$) and cultured for 10 days. SUSD2 High cardiac fibroblasts produced intact cardiac fibroblast derived extracellular matrix while SUSD2 Low cells do not produce an intact matrix. The results indicated that SUSD2 is a marker of cardiac fibroblast matrix competency.

Figure 3:
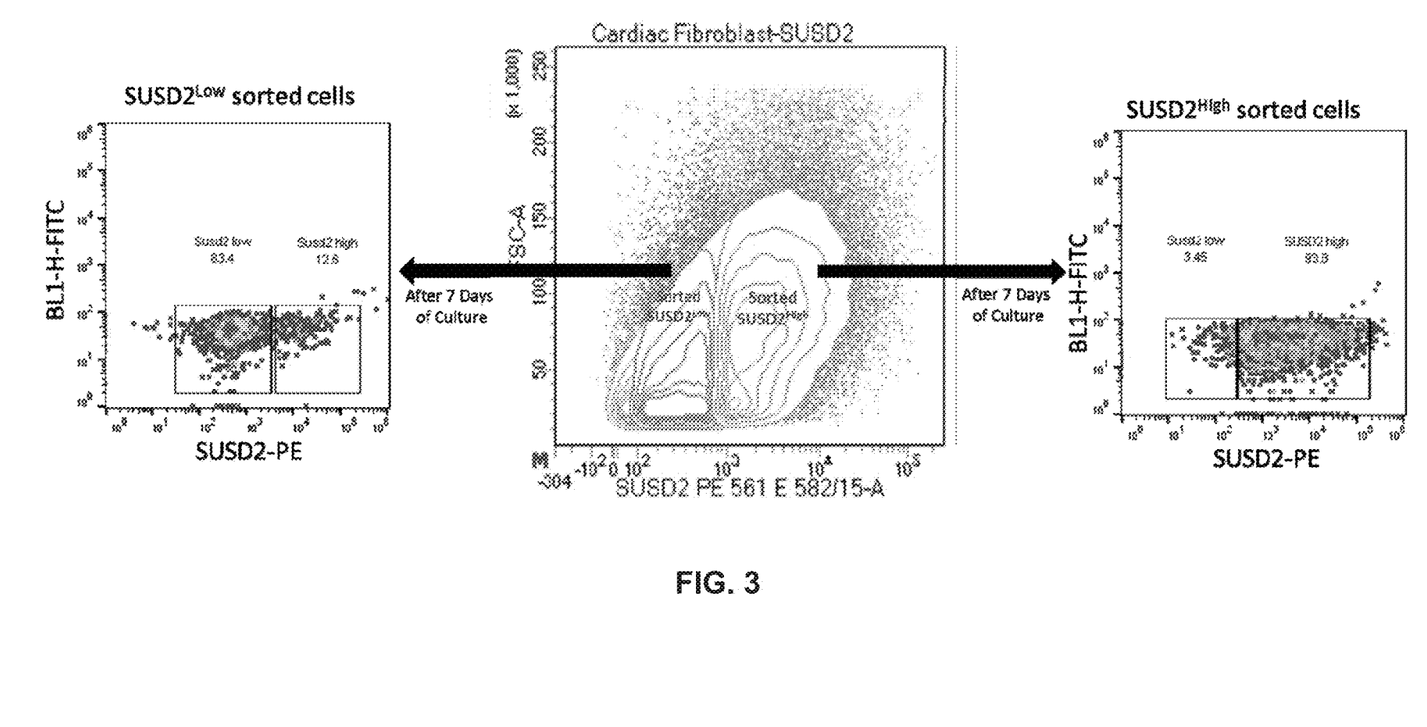
FIG. 3 shows stability of SUSD2 High and SUSD2 Low cardiac fibroblasts. Cardiac fibroblasts were sorted with flow cytometry based on their expression of SUSD2. The SUSD Low and SUSD2 High populations were plated and cultured under standard conditions for 7 days. The cells were then analyzed for SUSD2 expression by flow cytometry. Both the SUSD2 Low and SUSD2 High populations maintained a high level of purity. After 7 days, 83.4% of SUSD2 Low sorted cells maintained low SUSD2 expression phenotype based on MFI while 93.8% of SUSD2 High sorted cells maintained a high SUSD2 expression phenotype based on MFI.
Figure 4A:
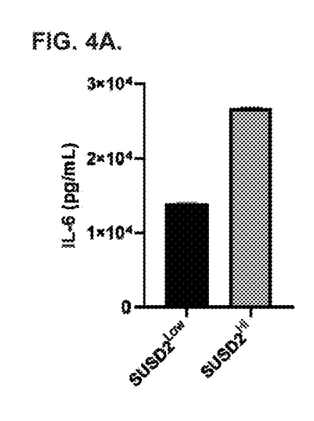
Figure 4B:
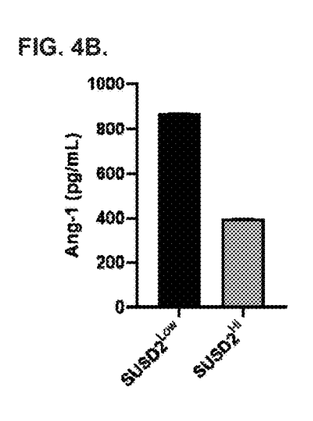
Figure 4C:
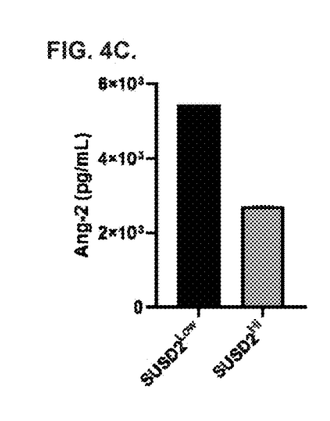
Figure 4D:
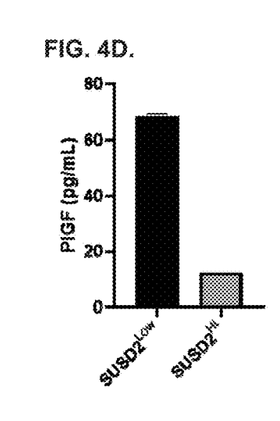
Figure 4E:
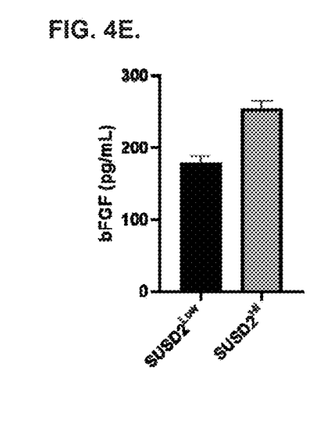
Figure 4F:
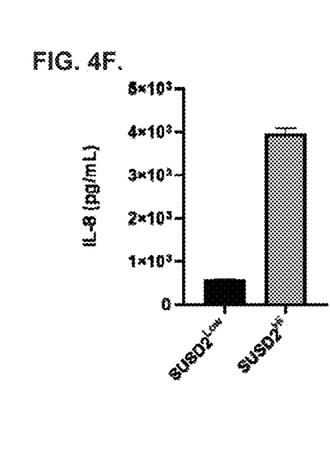
Figure 4G:
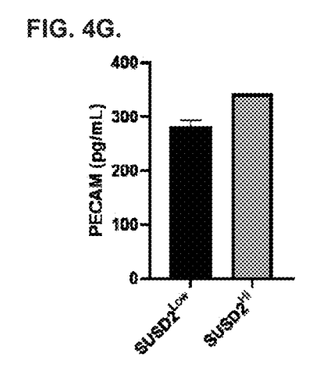
Figure 4H:
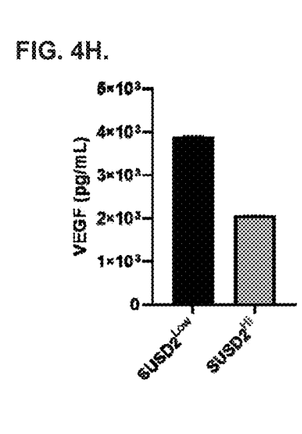
Figure 5:
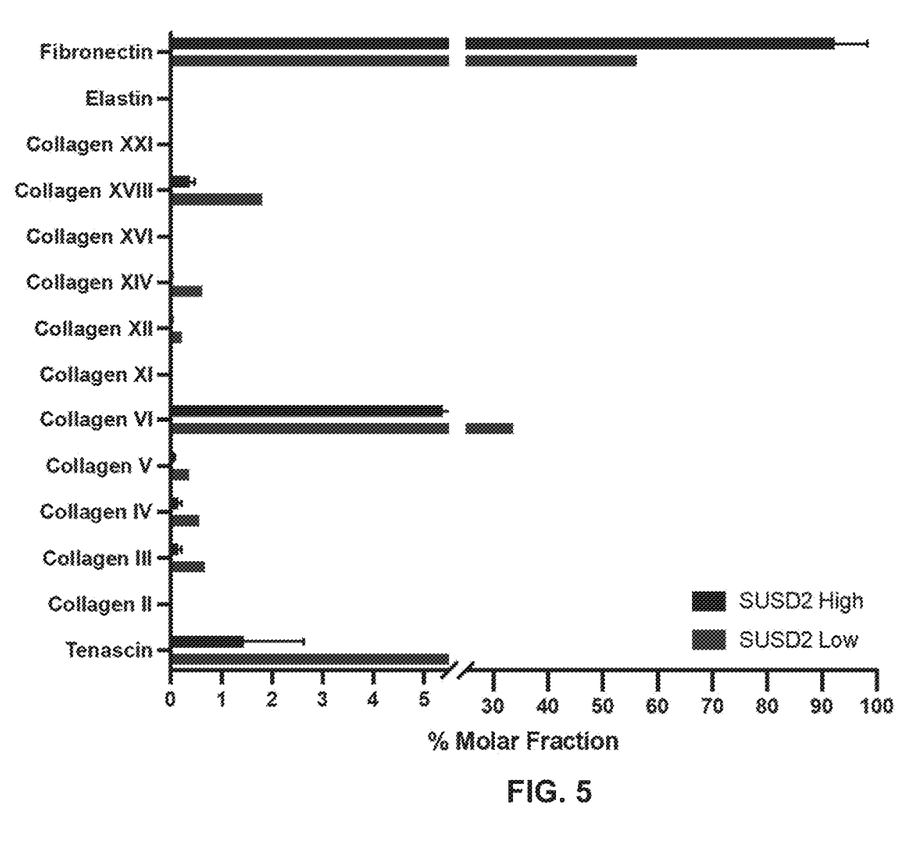
FIG. 5 illustrates the composition of CMF-ECM produced from High SUSD2 expressing cell strains (SUSD2 High) compared to SUSD2 low (SUSD2 Low) cell strains. The SUSD2 Low cell strains did not form intact scaffolds, which correlates with a reduced fibronectin expression in SUSD2 low (56%) compared to SUSD2 High (92%) cell strains.

As demonstrated in FIG. 3, both the SUSD2 Low and SUSD2 High populations maintained a high level of purity following culturing. Cardiac fibroblasts were sorted with flow cytometry based on their expression of SUSD2. The SUSD Low and SUSD2 High populations were plated and cultured under standard conditions (37° C., 5% CO$_2$, and 100% humidity) for 7 days. The cells were then analyzed for SUSD2 expression by flow cytometry. After 7 days 83.4% of SUSD2 Low sorted cells maintained low SUSD2 expression phenotype based on MFI while 93.8% of SUSD2 High sorted cells maintained a high SUSD2 expression phenotype based on MFI.

FIG. 4 demonstrates differences between SUSD2 High/Low cell populations for a cytokine secretome analysis done using a LegendPlex assay. This assay used antibody beads tagged with fluorochromes to detect secreted cytokines. Cardiac fibroblasts/myofibroblasts were sorted based on SUSD2 MFI expression (Low <500 MFI; High >500 MFI), equal numbers of SUSD2 High/Low cells were plated and cultured under standard culture conditions for 3 days. Media was sampled and analyzed for multiple analytes (cytokines). Significant differences in several cytokines were detected. The graphs above demonstrate that SUSD2 High/Low cell populations have very different secretome profiles, further indicating that these cell populations are distinctly different.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description can be made without departing from the spirit or scope of the present invention, as defined in the following claims.

The invention claimed is:

1. A method for preparing a cardiac extracellular matrix, comprising:
   (a) selecting SUSD2 High fibroblasts from a population of cardiac fibroblasts; and
   (b) plating the SUSD2 High fibroblasts into a culture having a cell density of 100,000 to 500,000 cells per cm$^2$, wherein the SUSD2 High fibroblasts secrete a cardiac extracellular matrix that is attached to the surface on which the SUSD2 High fibroblasts are plated.

2. The method of claim 1, wherein the selecting SUSD2 High fibroblasts from the population of cardiac fibroblasts comprises flow cytometry or immunofluorescence.

3. The method of claim 1 further comprising the steps of contacting the secreted cardiac extracellular matrix with ethylenediaminetetraaceticacid (EDTA), whereby the cardiac extracellular matrix becomes detached from the surface, forming a free floating bioscaffold.

4. The method of claim 1 further comprising the step of contacting the cardiac extracellular matrix with a decellularizing agent, whereby the cardiac extracellular matrix is decellularized.

5. The method of claim 4, wherein the decellularizing agent comprises peracetic acid, a mixture comprising ammonium hydroxide and octylphenol ethylene oxide (Triton™ X-100), or a mixture comprising Tri-N-Butyl-Phosphate and octylphenol ethylene oxide (Triton™ X-100).

6. The method of claim 1 further comprising the step of seeding the cardiac extracellular matrix with one or more cells that are therapeutic for cardiac disease or injury.

7. The method of claim 6, wherein the one or more cells that are therapeutic for cardiac disease or injury are selected from the group consisting of skeletal myoblasts, embryonic stem cells (ES), induced pluripotent stem cells (iPS), multipotent adult germline stem cells (maGCSs), bone marrow Mesenchymal stem cells (BMSCs), very small embryonic-like stem cells (VSEL cells), endothelial progenitor cells (EPCs), cardiopoietic cells (CPCs), cardiosphere-derived cells (CDCs), multipotent Is/1+ cardiovascular progenitor cells (MICPs), epicardium-derived progenitor cells (EPDCs), adipose-derived stem cells, human mesenchymal stem cells, human mesenchymal stem cells (derived from iPS or ES cells), skeletal myoblasts, exosomes or combinations thereof.

8. The method of claim 1 further comprising the step of seeding the cardiac extracellular matrix with one or more bioactive proteins that are therapeutic for cardiac disease or injury.

9. The method of claim 8, wherein the one or more bioactive proteins is a cytokine or a growth factor.

10. A method for preparing a cardiac extracellular matrix, comprising:
    (a) selecting SUSD2 High myofibroblasts from a population of cardiac myofibroblasts; and
    (b) plating the SUSD2 High myofibroblasts into a culture having a cell density of 100,000 to 500,000 cells per cm$^2$, wherein the SUSD2 High myofibroblasts secrete a cardiac extracellular matrix that is attached to the surface on which the SUSD2 High myofibroblasts are plated.

11. The method of claim 10, wherein the selecting SUSD2 High myofibroblasts from the population of cardiac myofibroblasts comprises flow cytometry or immunofluorescence.

12. The method of claim 10 further comprising the steps of contacting the secreted cardiac extracellular matrix with ethylenediaminetetraaceticacid (EDTA), whereby the cardiac extracellular matrix becomes detached from the surface, forming a free floating bioscaffold.

13. The method of claim 10 further comprising the step of contacting the cardiac extracellular matrix with a decellularizing agent, whereby the cardiac extracellular matrix is decellularized.

14. The method of claim 13, wherein the decellularizing agent comprises peracetic acid, a mixture comprising ammonium hydroxide and octylphenol ethylene oxide (Triton™ X-100), or a mixture comprising Tri-N-Butyl-Phosphate and octylphenol ethylene oxide (Triton™ X-100).

15. The method of claim 10, further comprising the step of seeding the cardiac extracellular matrix with one or more cells that are therapeutic for cardiac disease or injury.

16. The method of claim 15, wherein the or more cells that are therapeutic for cardiac disease or injury are selected from the group consisting of skeletal myoblasts, embryonic stem cells (ES), induced pluripotent stem cells (iPS), multipotent adult germline stem cells (maGCSs), bone marrow Mesenchymal stem cells (BMSCs), very small embryonic-like stem cells (VSEL cells), endothelial progenitor cells (EPCs), cardiopoietic cells (CPCs), cardiosphere-derived cells (CDCs), multipotent Is/1+ cardiovascular progenitor cells (MICPs), epicardium-derived progenitor cells (EPDCs), adipose-derived stem cells, human mesenchymal stem cells, human mesenchymal stem cells (derived from iPS or ES cells), skeletal myoblasts, exosomes or combinations thereof.

17. The method of claim 10 further comprising the step of seeding the cardiac extracellular matrix with one or more bioactive proteins that are therapeutic for cardiac disease or injury.

18. The method of claim 17, wherein the one or more bioactive proteins is a cytokine or a growth factor.

19. A method of generating a population of SUSD2 High fibroblasts, the method comprising selecting SUSD2 High fibroblasts from a population of cardiac fibroblasts to yield a population of SUSD2 High fibroblasts.

20. The method of claim 19, wherein the selecting SUSD2 High fibroblasts from the population of cardiac fibroblasts comprises flow cytometry or immunofluorescence.

21. A method of generating a population of SUSD2 High myofibroblasts, the method comprising selecting SUSD2 High myofibroblasts from a population of cardiac myofibroblasts to yield a population of SUSD2 High myofibroblasts.

22. The method of claim 21, wherein the selecting SUSD2 High myofibroblasts from the population of cardiac myofibroblasts comprises flow cytometry or immunofluorescence.

* * * * *